(12) United States Patent
Bitar et al.

(10) Patent No.: US 9,387,183 B2
(45) Date of Patent: Jul. 12, 2016

(54) METHOD OF TREATING DIABETES-RELATED IMPAIRED WOUND HEALING

(75) Inventors: Milad S. Bitar, Al-Yarmouk (KW); Fahd Al-Mulla, Al-Yarmouk (KW)

(73) Assignee: KUWAIT UNIVERSITY, Safat (KW)

( * ) Notice: Subject to any disclaimer, the term of this patent is extended or adjusted under 35 U.S.C. 154(b) by 64 days.

(21) Appl. No.: 13/339,353

(22) Filed: Dec. 28, 2011

(65) Prior Publication Data
US 2013/0172256 A1 Jul. 4, 2013

(51) Int. Cl.
| | | |
|---|---|---|
| *A61K 31/138* | (2006.01) | |
| *A61K 31/4535* | (2006.01) | |
| *A61K 31/565* | (2006.01) | |
| *A61K 38/19* | (2006.01) | |
| *A61K 9/00* | (2006.01) | |

(52) U.S. Cl.
CPC ........... *A61K 31/138* (2013.01); *A61K 31/4535* (2013.01); *A61K 31/565* (2013.01); *A61K 38/191* (2013.01); *A61K 9/0019* (2013.01); *G01N 2333/525* (2013.01); *G01N 2800/042* (2013.01); *G01N 2800/20* (2013.01)

(58) Field of Classification Search
CPC ............................... A61K 31/565; A61P 17/02
USPC .................................................. 514/9.4, 182
See application file for complete search history.

(56) References Cited

U.S. PATENT DOCUMENTS

| 6,262,021 | B1 | 7/2001 | Uvnäs-Moberg et al. |
| 6,319,907 | B1 | 11/2001 | Ferguson |
| 2006/0014679 | A1 | 1/2006 | Tojo et al. |

OTHER PUBLICATIONS

Siqueira et al. Imparied wound healing in mouse models of diabetes is medicated by TNF-alpha dysregulation and associated with enhanced activation of forkhead box 01 (FOX01). Diabetologia (2010) 53:378-388.*

Pincus et al. 17beta-Estradiol modifies diabetic wound healing by decreasing matrix metalloproteinase activity. Wounds 2010; 22(7): 171-178.*

Goren I et al, "Systemic anti-TNFalpha treatment restores diabetes-impaired skin repair in ob/ob mice by inactivation of macrophages," Journal of Investigative Dermatology, vol. 127(9), pp. 2259-2267 (2007).

Ishida Y et al, "Absence of IL-1 receptor antagonist impaired wound healing along with aberrant NF-κB activation and a reciprocal suppression of TGF-β signal pathway," Journal of Immunology, vol. 176(9), pp. 5598-5605 (2006).

Guo S. et al, "Factors affecting wound healing," Journal of Dental Research, vol. 89(3), pp. 219-229 (2010).

Lobman R et al, Proteases and the Diabetic Foot Syndrome: Mechanisms and Therapeutic Implications. Diabetes Care, vol. 28, pp. 461-471 (2005).

Fuentes L et al, "Inflammatory Mediators and Insulin Resistance in Obesity; Role of Nuclear Receptor Signaling in Macrophages," Mediators of Inflammation, vol. 2010 (2010)).

Campbell L et al, "Estrogen promotes cutaneous wound healing via estrogen receptor beta independent of its anti-inflammatory activities," Journal of Experimental Medicine, vol. 207(9), pp. 1825-1833 (2010).

Seno H et al, "Efficient colonic mucosal wound repair requires Trem2 signaling," Proceedings of the National Academy of Sciences, vol. 106(1), pp. 256-261 (2010).

Daley JM et al, "The phenotype of murine wound macrophages," The Journal of Leukocyte Biology, vol. 87(1), pp. 59-67 (2010).

Clowes JA et al, "Estrogen action on bone marrow osteoclast lineage cells of postmenopausal women in vivo," Osteoporosis International, vol. 20(5), pp, 761-769 (2009).

* cited by examiner

*Primary Examiner* — Jennifer M Kim
(74) *Attorney, Agent, or Firm* — Richard C. Litman

(57) ABSTRACT

The method of treating diabetes-related impaired wound healing includes the step of administering an effective amount of estrogen replacement therapy to a patient in need thereof to promote wound healing. Alternatively, the method of treating diabetes-related impaired wound healing includes the step of administering an effective amount of a TNF-α inhibitor to a patient in need thereof to promote wound healing. The method of treating diabetes-related impaired wound healing may also include both the step of administering an effective amount of estrogen replacement therapy and administering an effective amount of a TNF-α inhibitor to a patient in need thereof to promote wound healing.

3 Claims, 11 Drawing Sheets

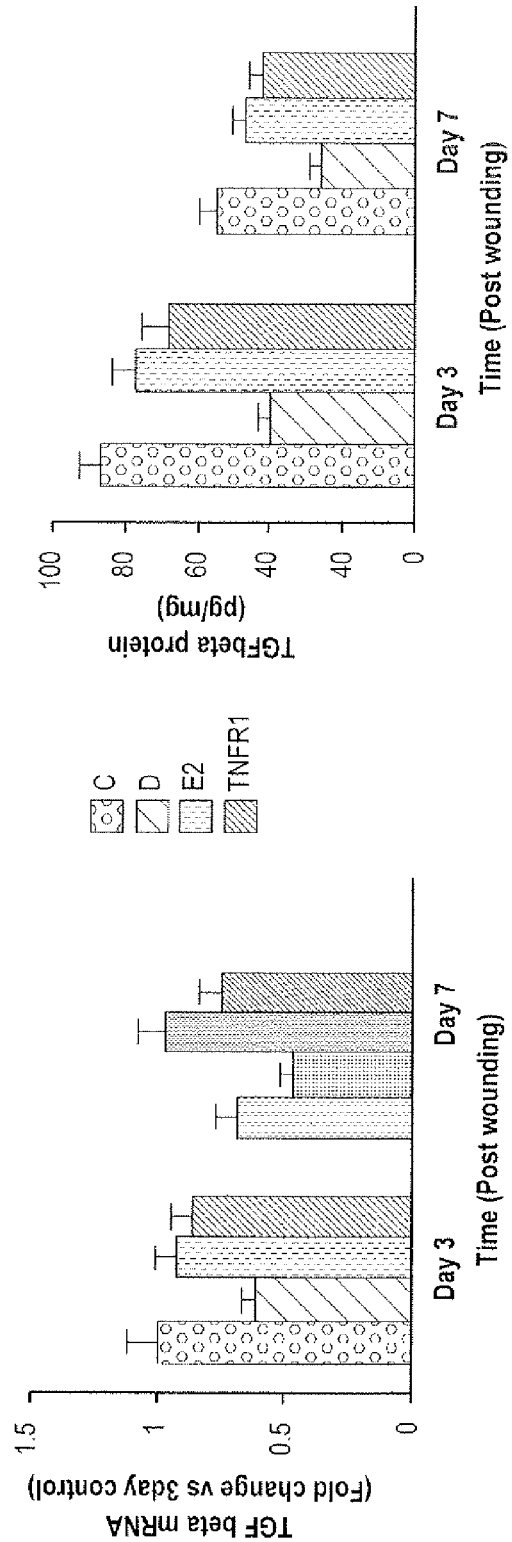
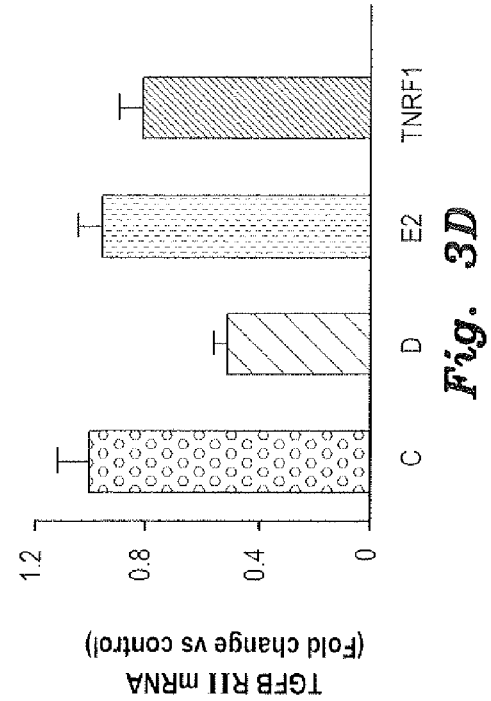
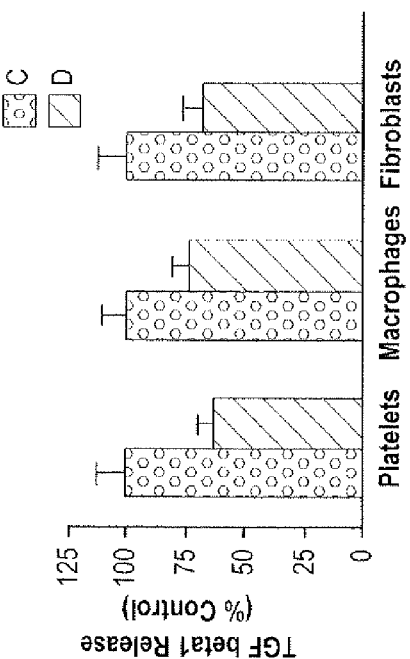
Fig. 3A
Fig. 3B
Fig. 3C
Fig. 3D

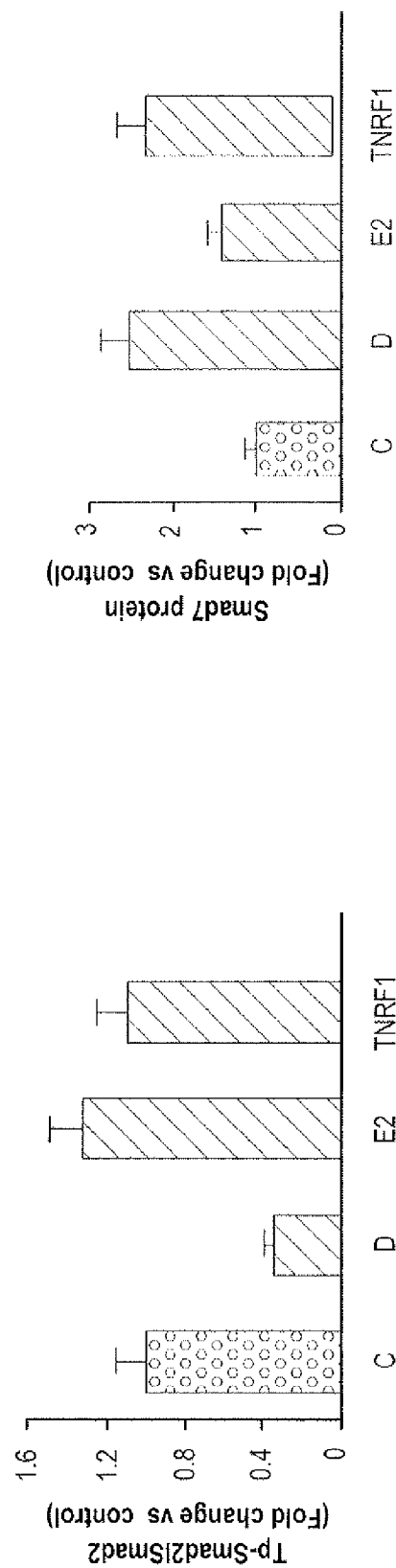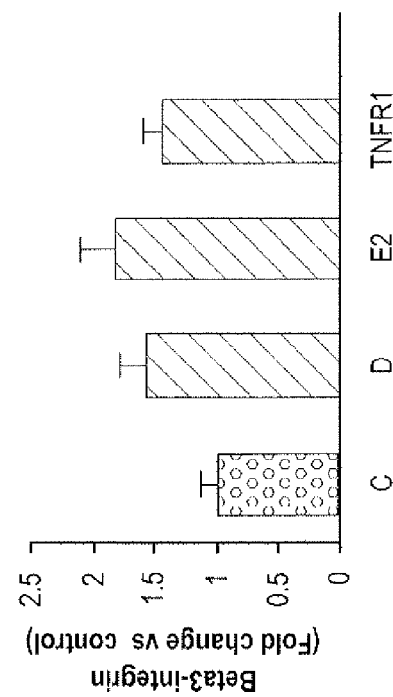

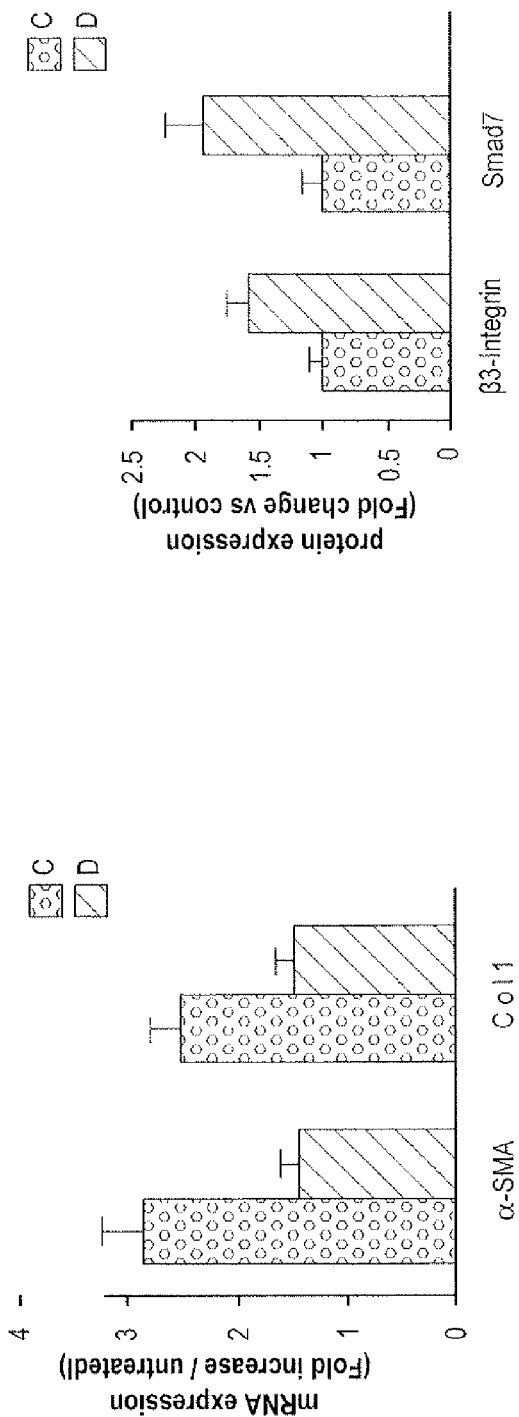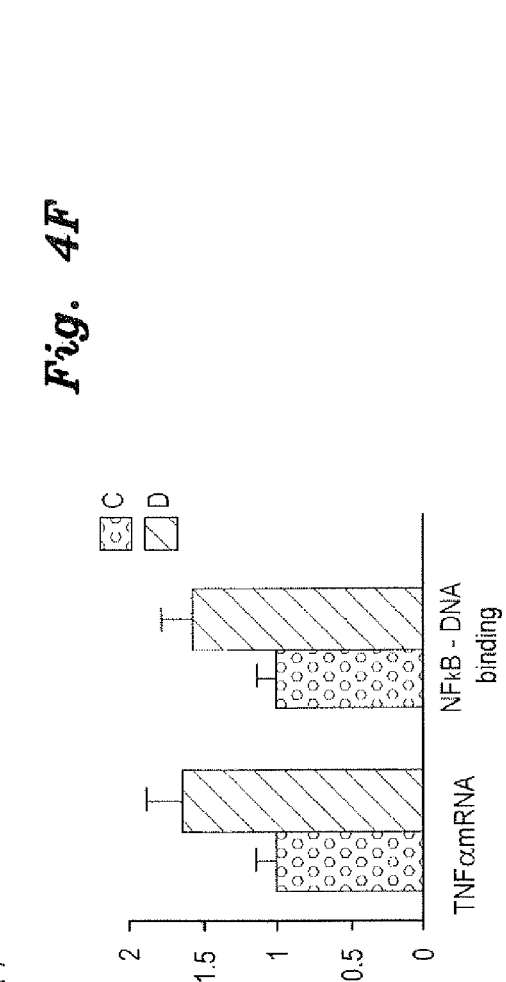

METHOD OF TREATING DIABETES-RELATED IMPAIRED WOUND HEALING

BACKGROUND OF THE INVENTION

1. Field of the Invention

The present invention relates to impaired wound healing, and particularly to a method of treating diabetes-related impaired wound healing.

2. Description of the Related Art

Proper cutaneous wound healing involves a progression of hemostasis/clotting, inflammation, cell proliferation and migration, and new tissue remodeling. This process depends on a multitude of inter- and intracellular signaling cascades. Typically the final steps of wound healing include closure several days to two weeks after injury, which is followed by remodeling of the new tissue. This process can be disrupted by stresses on the body, including patient habits, such as smoking and alcohol consumption, or by physical conditions, such as aging, stress, obesity and diabetes. Each of these factors impacts the normal processes involved in cutaneous cellular processes and signaling that are important to wound healing, and can result in a wound that suffers delayed or impaired wound healing, or in the worst case, a wound which fails to close at all.

Impairment of wound healing is a serious medical condition with enormous ramifications, and can lead to serious infection and amputation, for example. Non-healing cutaneous wounds affect 3 to 6 million Americans per year, with 85% of sufferers over the age of 65. Estimates of medical costs range in the billions of dollars per year in the US.

The processes of cell proliferation and migration are particularly important in normal wound healing. These processes are regulated by a balance of pro-inflammatory and anti-inflammatory signaling molecules in the wound environment. Pro-inflammatory cytokines, such as TNF-α, while important for fighting infection, can act antagonistically with anti-inflammatory cytokine growth factors, such as TGF-β, which promote cell proliferation, migration and differentiation. TNF-α influences the phenotype of macrophage immune cells, which change their secreted molecules in response to the presence of TNF-α to reinforce the inflammatory state and inhibit the cell migration/proliferation state within the wound.

Estrogen has also been shown to modulate the rate of wound healing. For example, the cutaneous wounds of post-menopausal women tend to heal more slowly than those of younger women, and estrogen replacement therapy (ERT) tends to ameliorate the slower rate of healing. Estrogen counteracts the effects of TNF-α and encourages cell proliferation and differentiation, partially through promoting an anti-inflammatory phenotype in which immune cells secrete TGF-β. Anti-inflammatory macrophages can be identified by the cytokines they secrete, as well as the pattern of protein receptors they display on their surface. TREM2 is a detectable receptor that is expressed on the surface of macrophages that exhibit an anti-inflammatory phenotype, but has only been observed in visceral tissue, such as adipocytes and colon tissue. Macrophages require exposure to the cytokines IL-4 and IL-13 before expressing TREM2. However, these cytokines are not expressed in cutaneous tissue. Changes in expression of TREM2 have been observed in diabetes, but only in adipocytes, where an upregulation was observed that was deemed causative in the etiology of the disease.

Thus, a method of treating diabetes-related impaired wound healing solving the aforementioned problems is desired.

SUMMARY OF THE INVENTION

The method of treating diabetes-related impaired wound healing includes the step of administering an effective amount of estrogen replacement therapy to a patient in need thereof to promote wound healing. Alternatively, the method of treating diabetes-related impaired wound healing includes the step of administering an effective amount of a TNF-α inhibitor to a patient in need thereof to promote wound healing. The method of treating diabetes-related impaired wound healing may also include both the step of administering an effective amount of estrogen replacement therapy and administering an effective amount of a TNF-α inhibitor to a patient in need thereof to promote wound healing.

The step of administering estrogen replacement therapy may comprise administering estrogen in the form of β-estradiol, raloxifene, tamoxifen, or a combination thereof. The step of administering a TNF-α inhibitor may comprise administering PEG-sTNF-R1 to the patient. The method may also comprise the steps of monitoring the patient's estrogen levels and adjusting the dosage level of the estrogen replacement therapy accordingly, and/or monitoring the levels of cytokines and macrophage phenotypes in tissue samples taken from the site of the wound and adjusting the dosage of the TNF-α inhibitor to ensure a proper balance between TNF-α and TNF-β response of the patient's immune system to the wound.

These and other features of the present invention will become readily apparent upon further review of the following specification and drawings.

BRIEF DESCRIPTION OF THE DRAWINGS

FIG. 3A is a chart showing relative TGF-β mRNA transcription in wounds at 3 days and 7 days in normal and diabetic rats, as well as in diabetic rats exposed to estradiol or TNF-α inhibitor.

FIG. 3B is a chart showing relative TGF-β protein in wounds at 3 days and 7 days in normal and diabetic rats, as well as in diabetic rats exposed to estradiol or TNF-α inhibitor.

FIG. 3C is a chart showing relative amounts of TGF-β secreted from various cell types isolated from wounds at 3 days and 7 days in normal and diabetic rats, as well as diabetic rats exposed to estradiol or TNF-α inhibitor.

FIG. 3D is a chart showing relative TGF-β RII mRNA transcription in wounds at 7 days in normal and diabetic rats, as well as diabetic rats exposed to estradiol or TNF-α inhibitor.

FIG. 3E is a chart showing the relative ratio of phosphorylated Smad2 to total Smad2 in wounds at 7 days in normal and diabetic rats, as well as diabetic rats exposed to estradiol or TNF-α inhibitor.

FIG. 3F is a chart showing relative Smad7 protein levels in wounds at 7 days in normal and diabetic rats, as well as diabetic rats exposed to estradiol or TNF-α inhibitor.

FIG. 3G is a chart showing relative β-3 integrin in wounds at 7 days in normal and diabetic rats, as well as diabetic rats exposed to estradiol or TNF-α inhibitor.

FIG. 4E is a chart showing smooth muscle actin (α-SMA) and collagen1 (Col1) mRNA transcription is attenuated in TGF-β-treated rat diabetic fibroblasts versus TGF-β-treated control fibroblasts.

FIG. 4F is a chart showing that expression of β-3 integrin and Smad7 are upregulated in rat diabetic fibroblasts versus control fibroblasts.

FIG. 4G is a chart showing that transcription of TNF-α and NFκB DNA-binding activity are upregulated in rat diabetic fibroblasts versus control fibroblasts.

Similar reference characters denote corresponding features consistently throughout the attached drawings.

DETAILED DESCRIPTION OF THE PREFERRED EMBODIMENTS

Figure 1A:
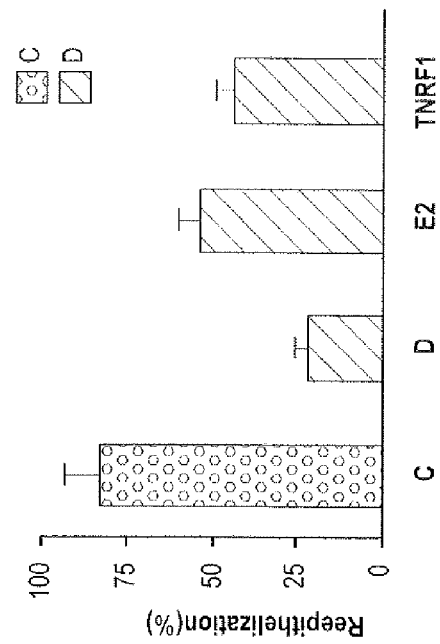
FIG. 1A is a chart showing percentage wound closing in normal and diabetic rats, as well as in diabetic rats exposed to estradiol or TNF-α inhibitor, at days 3 and 7 after wounding.

The method of treating diabetes-related impaired wound healing includes the step of administering an effective amount of estrogen replacement therapy to a patient in need thereof to promote wound healing. Alternatively, the method of treating diabetes-related impaired wound healing includes the step of administering an effective amount of a TNF-α inhibitor to a patient in need thereof to promote wound healing. The method of treating diabetes-related impaired wound healing may also include both the step of administering an effective amount of estrogen replacement therapy and administering an effective amount of a TNF-α inhibitor to a patient in need thereof to promote wound healing.

The step of administering estrogen replacement therapy may comprise administering estrogen in the form of β-estradiol, raloxifene, tamoxifen, or a combination thereof. The step of administering a TNF-α inhibitor may comprise administering PEG-sTNF-R1 to the patient. The method may also comprise the steps of monitoring the patient's estrogen levels and adjusting the dosage level of the estrogen replacement therapy accordingly, and/or monitoring the levels of cytokines and macrophage phenotypes in tissue samples taken from the site of the wound and adjusting the dosage of the TNF-α inhibitor to ensure a proper balance between TNF-α and TNF-β response of the patient's immune system to the wound.

The inventors have found that impaired wound healing, associated, for example, with diabetes, is, in some cases, the result of estrogen deficiency, as well as TNF-α overexpression, which induces a condition of chronic inflammation. This inflammation can impair the normal processes of wound healing. The combination of a low estrogen and high TNF-α environment acts to impair the proper functions of cell migration, proliferation and differentiation.

The inventors have found that a mechanism for impaired wound healing might be their combined effect on TGF-β signaling. Whatever the underlying mechanism(s), the TNF-α inhibitors or estrogen receptor agonists, considered singly, but especially in combination, exert an influence on fibroblast and macrophage phenotype, the course of inflammation and the rate of wound healing. In particular, macrophages display a range of phenotypes that proliferate at a rate induced by the signals they encounter in their environment. In simplistic terms macrophages exhibit a classical/M1 (or pro-inflammatory) phenotype or an alternative/M2 (or anti-inflammatory) phenotype. Each phenotype is keyed to a different role in the healing response. The inventors have found that particular macrophage phenotypes can be identified by particular biomarkers on their surface or that they secrete. Through their studies of TGF-β signaling in tissues derived from impaired wounds, they have correlated defects in this signaling with impaired wound healing and with particular macrophage phenotypes.

Lastly, the inventors have shown that TNF-α inhibitors and estrogen receptor agonists may restore proper function of TGF-β signaling in wounds exhibiting impaired healing. Thus, the inventors arrived at the insight that TNF-α inhibitors, such as PEG-sTNF-R1 and estrogen receptor agonists (including β-estradiol, raloxifene and tamoxifen) can achieve synergistic function in improving the healing of cutaneous wounds. Additionally, the effect of these therapeutics can be monitored through monitoring the expression of wound macrophage markers, such as transforming growth factor beta (TGF-β), interleukin 1 receptor antagonist (IL-1ra), triggering receptors expressed on myeloid cells 2 (TREM2), tumor necrosis factor alpha (TNF-α), macrophage inhibitory factor (MIF), and myeloperoxidase (MPO). Cytokines can be monitored by methods that are known in the art, for example, western blot, ELISA, immunofluorescence, quantitative real-time PCR, northern blot, and microscopy. Expression levels can be compared to those exhibited by cells derived from normally healing wounds; in particular, the expression of TREM2 in macrophages derived from impaired healing wounds may fall to less than 70% of levels of that in macrophages derived from normally healing wounds. Levels of about 50% are typical in diabetics exhibiting impaired wound healing, but expression can be so low as to be unobservable. Trem2 expression can be observed by quantitative PCR (polymerase chain reaction). Methods for performing quantitative PCR are known in the art. Additionally, TREM2 antibodies exist and can be used to quantitatively determine protein expression by methods known in the art.

IL-1ra expression can also be less than 70% in diabetics, but typically about 50% of the expression found in normally healing wounds is indicative of impaired wound healing. TNF-α inhibitors and estrogen receptor agonists can return TREM2 expression and IL-1ra expression to about equal to the expression observed in normally healing wounds. TGF-β expression can be about 30% lower in cells derived from impaired healing wounds, but an efficacious amount of estrogen receptor agonist and TNF-α inhibitor can return TGF-β expression to about that of cells derived from normally healing wounds.

MPO expression can be about 2 to 4-fold higher in wounds that suffer from impaired healing. These levels of MPO will return to about equal upon an efficacious administration of estrogen receptor agonist and TNF-α inhibitor. Furthermore MIF expression is about 2-5 fold higher in cells derived from cutaneous wounds exhibiting impaired healing characteristics, but return to levels about equal to those of normally healing cutaneous wounds upon efficacious administration of estrogen receptor agonists and TNF-α inhibitors.

In the method of treating diabetes-related impaired wound healing, estrogen can be delivered by methods well known in the art. For example, estradiol (E2) can be delivered by insertion of a subcutaneous delayed release device in doses already clinically available. It can also be delivered topically, including through a transdermal drug delivery system ("patch") or a spray, all of which are known in the art. Selective estrogen replacement therapy (SERM) can also be delivered orally. Estrogen replacement therapy may also include the estrogen receptor agonists raloxifene and tamoxifen TNF-α inhibitors can also be delivered orally, intravenously, intramuscularly, subcutaneously, or topically at the site of the wound. PEG-sTNF-R1 is usually delivered by injection, e.g. subcutaneously. The dosage of PEG-sTNF-RI injected per week can be between 100 μg/kg and 2000 μg/kg in a human, but more preferably between 300 μg/kg and 1500 μg/kg, and most preferably between 600 μg/kg and 900 μg/kg per week. The weekly dosages can be administered at any interval, for example once per week, but are most preferably administered 3 times per week in evenly spaced intervals that aggregate to the total weekly dose.

The following summarizes studies conducted by the inventors that provide the experimental basis for the method of treating diabetes-related wound healing. Experimental materials and procedures include the following.

All animal procedures were performed in accordance with the NIH Guidance for the Care and Use of Laboratory Animals. The current study used the mildly hyperglycemic, non-obese Goto-Kakizaki (GK) spontaneously diabetic rats, produced by selective inbreeding of glucose-intolerant Wistar rats as a genetic model for type 2 diabetes. Weight-matched female Wistar rats (Kuwait University breeding colony) served as controls. All animals were maintained under standard conditions with 12 hours on/off light cycle, commercial diet, and water ad libitum. Rats destined for various experimental manipulations, including wounding, insulin sensitivity, and drug treatment, were initially matched with regard to body weight (e.g., 230 to 250 g), plasma levels of glucose, free fatty acids and insulin. These indices are commonly used to reflect the severity of the diabetic state.

Animals used for insulin sensitivity (n=5-7/group) and WH (n=8-10) studies were partitioned into several experimental groups, including controls, diabetics, and diabetics plus either β-estradiol (E2) or the soluble pegylated form of the TNF receptor blocker (PEG-sTNF-RI, Amgen, Thousand Oaks, Calif.).

The estrogen replacement therapy included the subcutaneous insertion of a slow-release pellet (1.5 mg E2/pellet, 60 days release, Innovative Research of America), which resulted in a maximal serum E2 level (~75 pg/ml) resembling that of cyclic control rats during the period of proestrus. Cycling control rats in proestrus were used as a reference group. Similarly, the diabetic rats were also treated with PEG-sTNF-RI, a soluble long-lasting form of TNF-RI that neutralizes TNF-α action. Preclinical studies have shown that subcutaneous administration of PEG-sTNF-RI appears to limit the inflammatory reaction of rheumatoid arthritis in rat models at a dose of 0.3 mg/kg. The course of therapy most effective in the current WH study was 1.5 mg/kg of PEG-sTNF-RI administered subcutaneously three times per week. All of the treatment regimens used with the diabetic rats were given for at least three weeks before wound initiation, and this form of treatment continued during the course of wound healing.

Animals in each experimental group were Ketanest/Rompun-anesthetized, and six full-thickness excisional wounds (8 mm in diameter), equidistant from the midline, were aseptically inflicted in the shaved, povidine-iodine washed dorsal skin. Wounds were photographed at 0, 3, and 7 days after wounding using a Sony D-9 digital camera. Images of the wound area were visualized and measurements were taken using Adobe Photoshop (version 7.0; Adobe Systems). The percentage of wound closure at each time point was calculated using the following formula: (1−[current wound size/initial wound size])×100.

Animals were sacrificed at 3 and 7 days post-wounding. An area that included the complete epithelial margins was excised, and the wounds were bisected and processed so that the mid-point of the wound was sectioned and compared between groups. The resulting specimens were either fixed in 4% paraformaldehyde in phosphate-sucrose buffer and analyzed histologically, or flash frozen in liquid nitrogen and stored at −80° C. prior to biochemical analysis, or embedded in Optimum Cutting Temperature (OCT) compound and immediately frozen in liquid nitrogen for immunofluorescence analysis. It is worthy of note that the number of wounds used for most of the aforementioned studies were in the range of 48 to 60 wounds per treatment. Some parameters related to sex hormones and oxidative stress were measured in serum or wound fluids, which were collected on day 7 post-wounding from subcutaneously inserted stainless steel mesh chambers.

Clamp experiments can be conducted by numerous methods known in the art, but a typical Rapid Insulin Sensitivity Test protocol comprises a 5-minute intravenous insulin bolus (total 50 milliUnits (mU)/kg body weight), and glucose at a concentration of 100 mg/ml is infused intravenously at a rate of 5 mg glucose per kg body weight per minute. Blood can be drawn at a desired interval, for example, every 2 min to measure blood glucose. The rate of glucose infusion is adjusted to maintain normoglycemia. Infusion is suspended when no more glucose is required to maintain normoglycemia, and the total amount of glucose infused in response to the known bolus of insulin is calculated (the RIST index). The current studies characterize the insulin sensitivity of GK rats in the context of E2 and TNF-RI therapy.

Primary rat dermal fibroblasts (RDFs) were obtained from the dorsal skin of control and GK diabetic rats. After sterilization in povidine solution, the rat skin was washed in sterile water and rinsed in 70% ethanol in PBS. Epidermis and dermis were separated following overnight incubation in 0.25% Trypsin/EDTA at 4° C. Dermis was cut into small fragments and incubated in Dulbecco's modified Eagle medium (DMEM; Invitrogen) containing collagenase type I (250 U/ml; Sigma) for thirty minutes at 37° C. in 5% $CO_2$ with constant agitation. The fragments were triturated vigorously to release fibroblasts, which were collected by centrifugation. The cell pellet was washed twice with PBS, re-suspended in complete medium (DMEM supplemented with 10% fetal calf serum, Invitrogen), penicillin (100 U/ml), and streptomycin (100 µg/ml)), 2 mM L-glutamine and 26 mM HEPES and then cultured under standard conditions (humidified 5% $CO_2$, 37° C.). Human dermal fibroblasts (HDFs) from healthy (AG04447) and diabetic donors (AG06084), matched with regard to sex (male) and age (healthy, 35 YR; diabetic, 41 YR), were obtained from the Coriell Institutes for Medical Research (Camden, N.J.) and cultured using the same protocol described above for RDFs. Treatment with TGF-β was carried out in serum-free media to avoid the possibility that serum components might differentially affect some of the assays used in this study.

An in vitro wound healing assay was conducted on cultured fibroblasts obtained from control and diabetic rats and grown to confluence in 6-well plates in DMEM medium containing 10% serum. Medium was removed, and cells were washed with Hank's medium and then cultured for 24-hr in serum-free medium plus 0.2% BSA (SFM). The monolayer was artificially injured by scratching across the plates with a sterile pipette tip, washed twice with Hank's medium to remove the floating cells, and then cultured for 24-hr in SFM containing mitomycin C (10 µg/ml, to prevent proliferation). Images of the same areas were taken immediately after scratching (time point 0) and 24-hr thereafter using an Axiocam digital camera mounted on an Axiovert 40 C(Ziess) phase-contrast microscope. Scratched wound area was assessed using Axiovision version 4.6.3 software, and percent area of wound closure at each time point was calculated using the following formula: (1−[current wound size/initial wound size])×100.

The above protocol was also conducted on a keratinocyte cell line in which cell migration was measured in response to a conditioned medium of fibroblast of type 2 diabetes.

For the assessment of macrophage recruitment and angiogenesis, frozen OCT-embedded wound sections were fixed with 4% paraformaldehyde for 15 minutes, washed with PBS, permeabilized with 0.25% Triton X-100 or 100 µmol/l digitonin for 10 minutes, washed with PBS, and blocked with 2% BSA in PBS-Tween 20 for 30 minutes at room temperature. The sections were incubated with the appropriate primary antibody (rabbit, mouse in 1% BSA, overnight). These antibodies included anti-CD68 (Serotech), anti-CD31 (Santa Cruz), and anti-vimentin (Santa Cruz) to assess the recruitment of macrophages, endothelial cells and fibroblasts, respectively. After incubation with fluorochrome-conjugated secondary antibodies (Alexa Fluor 555 or Alexa Fluor 488, Invitrogen) at room temperature for 30 minutes, the sections were treated with DAPI-antifade (B-tect), and then examined using a fluorescence confocal microscope system (LSM Meta 510, Zeiss, Germany).

To assess key molecular and biochemical components, wound specimens were frozen in liquid nitrogen and were powdered and homogenized for RNA extraction or protein-based differential centrifugation. The resulting samples were assessed in terms of collagen content (collagen type I, hydroxyproline), TGF-β/Smad-dependent signaling (TGF-β RII, p-Smad2, Smad7), and for the expression of classical- (TNF-α, MIT) and alternative-(IL-1ra, Trem2, TGF-β1) macrophage activation markers using RT-PCR-, western blotting-, ELISA- and spectrophotometric-based techniques.

To perform quantitative gene expression analysis, total RNA was extracted using TRIZOL (Invitrogen) and further purified using RNeasy MinElute Cleanup Kit (Qiagen). RNA (5 µg) was reverse transcribed (SuperScript III, Invitrogen), and the expression of collagen I and the various alternative/classical-macrophage markers were analyzed using pre-developed Q-RT-PCR assays (Assay on Demand, Applied Biosystems). PCR reactions were performed in a 25 µl reaction volume containing cDNA using the Assay on Demand of the target genes, TaqMan universal master mix, and the 18S rRNA internal control. Amplification and detection of specific products were determined using an ABI PRISM 7500 sequence detection system (Applied Biosystems). Relative expression of real-time PCR products was determined by using the ΔΔCt method to compare target gene and housekeeping gene mRNA expression. In most cases, the data were expressed as the fold of change vs the 3-day control wounds, which were given the value of 1. A statistical comparison between various experimental groups was conducted within each time point during the course of wound healing.

To assess protein expression and NF-κB activation, frozen liquid nitrogen powdered wounded tissues or serum starved RDFs/HDFs were homogenized on ice in a RIPA buffer (50 mM Tris pH 7.4, 150 mM NaCl, 10 mM EDTA, 2 mM sodium vanadate, 150 mM sodium fluoride, 0.5% sodium deoxycholate, 1% Triton X-100, and a cocktail of protease inhibitors) for total cellular proteins, or with a hypotonic buffer A (10 mM HEPES pH 7.9, 10 mM KCl, 2 mM MgCl2, 0.1 mM EDTA, 1.0 mM DTT, 0.5 mM PMSF, 20 mM NaF, 1 mM sodium orthovanadate and a cocktail of protease inhibitors) for the nuclear protein extraction. The RIPA buffer-dependent homogenates were centrifuged at 13,000×g for 15 minutes at 4° C., and the resulting supernatants were collected and stored at −80° C. Similarly, the hypotonic buffer-dependent homogenates (500 µl) were incubated on ice for 20 minutes, after which 50 µl of 10% NP-40 was added. The mixture was vortexed and centrifuged (5000×g, 1 min, 4° C.). The crude nuclear pellets were re-suspended in 150 µl buffer B containing 20 mM HEPES (pH 7.9), 400 mM NaCl, 0.1 mM EDTA, 1.5 mM MgCl2, 1 mM DTT, 0.5 mM PMSF, 20 mM NaF, 1 mM sodium orthovanadate, 25% glycerol and a cocktail of protease inhibitors, incubated on ice for 45 minutes with intermittent mixing, and centrifuged (12,000×g, 25 min, 4° C.). The resulting supernatants representing nuclear proteins were stored at −80° C.

Samples of the total cellular and nuclear extracts were subjected to protein determinations using the Bicinchoninic Acid Protein Assay Kit (Pierce). For western blotting, an equal volume of 2×SDS sample buffer was added, and the samples were denatured by boiling for 5 minutes. Proteins were applied to SDS-polyacrylamide gel electrophoresis (SDS-PAGE) and transferred to an Immobilon polyvinylidene difluoride membrane (BioRad). The membranes were blocked with tris buffered saline containing 0.05% Tween 20 and 5% skim milk, and then treated with a number of primary antibodies, including Smad2/p-Smad2 (Cell Signaling), Smad7 (Imgenex), and β3-integrin (Santa Cruz). Protein bands were visualized by chemiluminescence (Pierce), and band intensity was determined using Bio-Rad densitometer. Unless otherwise specified, β-actin was used to standardize the quantity of sample protein for all Western blotting analyses.

A quantitative analysis of p65-DNA binding activity was performed on the nuclear protein extracts using the ELISA-based TransAM NFκB Transcription Factor Assay Kit (Active Motif) according to the manufacturer's instruction. Briefly, samples containing an equal amount of nuclear proteins were incubated in 96-well plates coated with an oligonucleotide containing the NF-κB consensus-binding site. The activated transcription factor, specifically bound to the immobilized oligonucleotide, was detected using an antibody directed against NF-κB and a secondary antibody conjugated to horseradish peroxidase. The developing solution was then added, and the OD (450-665 mm) was measured using a microplate reader (Thermo Scientific). Results were expressed as % of control.

To assay protein components of wound samples, spectrophotometric and ELISA-based methods were used. For the ELISA assay, wound fluid samples were homogenized with PBS containing a protease inhibitor cocktail (Roche Diagnostic), centrifuged (12,000×g, 10 min), and the resulting supernatants were used for the determination of TGF-β1, IL-1β (R&D Systems), VEGF, and TNF-α (Ray-Biotech) with commercial ELISA kits according to the manufacturer's instructions. Similarly, ELISA-based assays were also used in the assessment of serum and wound fluid contents of E2 (Cayman), testosterone (Oxford Biomedical research), insulin (Alpco) and F2 isoprostanes (Assay Design). Total protein in the supernatants was measured with a commercial kit (Bicinehoninic Acid Protein Assay Kit, Pierce). Wound hydroxyproline and myeloperoxidase (MPO) contents were determined according to art-accepted methods.

Data are expressed as mean±SEM. The Mann-Whitney U-test was used for determining the level of significance of differences between samples, and Bonferroni's test was instituted for multiple comparisons. A level of P≤0.05 was considered to be significant.

EXAMPLE 1

GK rats were characterized according to physical traits. Rats in each experimental group exhibited similar gains in body weight over the duration of the study (~30 days, Table 1). Levels of testosterone and key indices of oxidative stress (e.g., $F_2$ isoprostanes) in plasma and wound fluids (exudates containing serum/tissue derived components, a reflector of wound microenvironment) were elevated as a function of diabetes (Table 1). In contrast, uterine weights and plasma and wound microenvironment E2 levels were decreased in this disease state (Table 1). Most of the aforementioned abnormalities were normalized following ERT (estrogen replacement therapy).

TABLE 1

Global Physiological Characteristics of Diabetic Rats

| Parameters | C | D | D + E2 | D + TNFR1 |
|---|---|---|---|---|
| Weight (g) | | | | |
| Body | 235 ± 10 | 221 ± 8 | 238 ± 12 | 225 ± 9 |
| Uterus | 0.48 ± 0.04 | 0.21 ± 0.02* | 0.41 ± 0.04** | N.D. |
| Plasma (pg/ml) | | | | |
| Estrogen | 78 ± 8.9 | 27 ± 3.5* | 69 ± 7.0** | N.D. |
| Testosterone | 321 ± 27 | 887 ± 77* | 849 ± 85* | N.D. |
| $F_2$ Isoprostanes | 37 ± 4.2 | 122 ± 10.8* | 47 ± 6.6** | 69 ± 8.4** |
| Wound fluid (pg/ml) | | | | |
| Estrogen | 47 ± 4.5 | 24 ± 3.2* | 44 ± 5.7** | N.D. |
| Testosterone | 218 ± 29 | 498 ± 55* | 456 ± 47* | N.D. |
| $F_2$ Isoprostanes | 33 ± 3.1 | 91 ± 7.1* | 43 ± 4.4** | 59 ± 5.2** |

C: Control;
D: Diabetic;
D + E2; Diabetic treated with estrogen;
D + TNFR1: Diabetic treated with PEG-sTNF-R1
*Significantly different from corresponding control values at P ≤ 0.05
**Significantly different from corresponding diabetic values at P ≤ 0.05

Fasting plasma levels of glucose and insulin were higher in diabetic rats than in corresponding control rats (Table 2). Similarly, post-clamp plasma insulin levels were also increased in these animals (Table 2). Treatment of diabetic animals with E2 or the PEG-sTNF-RI partially ameliorated the hyperinsulinemic state (Table 2) and significantly improved target tissue sensitivity to insulin, as exemplified by the increase in the glucose infusion rate (Table 2). These data support the notion that TNFRI or ERT seems to exert a favorable effect on carbohydrate tolerance (Table 2).

TABLE 2

ERT/PEG-sTNF-R1 Enhance Insulin Sensitivity in Female Diabetic Rats

| Parameters | Test Group | | | |
|---|---|---|---|---|
| | C | D | D + E2 | D + TNFR1 |
| FBG (mg/dl) | 83 ± 9 | 142 ± 13* | 131 ± 16 | 125 ± 17 |
| FPI (ng/ml) | 0.59 ± 0.05 | 1.06 ± 0.12* | 0.63 ± 0.06** | 0.68 ± 0.05** |
| PCPI (ng/ml) | 3.15 ± 0.31 | 7.87 ± 0.6* | 4.18 ± 0.5* | 4.61 ± 0.4** |
| GIR (mg/min/kg body wt) | 21.5 ± 2.5 | 12.7 ± 1.37* | 19.55 ± 1.55** | 18.53 ± 1.49** |

FBG: Fasting blood glucose;
FPI: Fasting plasma insulin;
PCPI: Post clamp plasma insulin;
GIR: Glucose infusion rate
C: Control;
D: Diabetic;
D + E2: Diabetic treated with estrogen
D + TNFR1: Diabetic treated with PEG-sTNFR1
*Significantly different from corresponding control values at P ≤ 0.05
**Significantly different from corresponding diabetic values at P ≤ 0.05

EXAMPLE 2

Figure 1B:
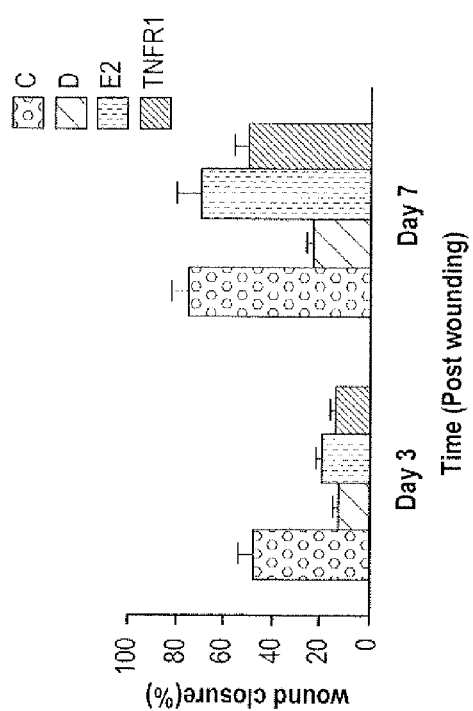
FIG. 1B is a chart showing percentage re-epithelialization in wounds at day 7 in normal and diabetic rats, as well as diabetic rats exposed to estradiol or TNF-α inhibitor.

This study demonstrates that delayed wound healing in lean, non-obese Type 2 diabetic animals reflects impaired re-epithelialization, re-dermalization, and granulation tissue formation. To investigate whether non-obese, slightly hyperglycemic GK rats display delayed WH, these animals and their control counterparts were subjected to full-thickness excisional wounding using a dermal punch. In control animals, wound areas were reduced with linear kinetics throughout the 7 clays of observations, at the end of which over 70% closure was documented. In contrast, a delay in wound closure was a characteristic feature of the GK diabetic rats (FIG. 1A). Wound closure was also monitored histologically. In control rats, re-epithelialization was about 78% at 7 days after wounding. In contrast, a diminution in the rate of re-epithelialization was evident as a function of diabetes (FIG. 1B). These observations indicate that wound closure and eventual healing were impaired in the GK diabetic rats.

Figure 2A:
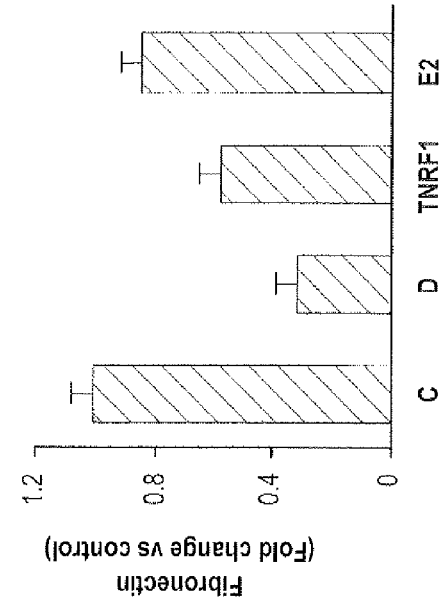
FIG. 2A is a chart showing relative fibronectin mRNA transcription in wounds at 3 days in normal and diabetic rats, as well as in diabetic rats exposed to estradiol or TNF-α inhibitor.
Figure 2B:
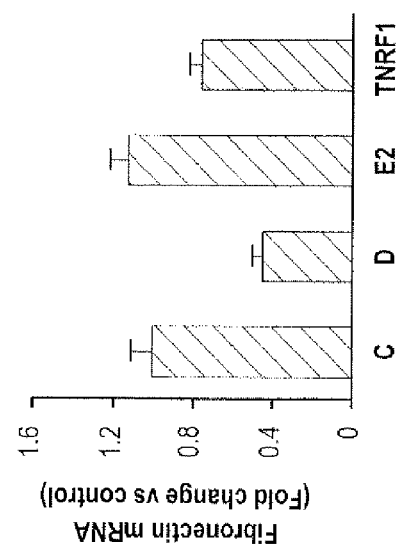
FIG. 2B is a chart showing relative fibronectin protein accumulation in wounds at 3 days in normal and diabetic rats, as well as in diabetic rats exposed to estradiol or TNF-α inhibitor.
Figure 2C:
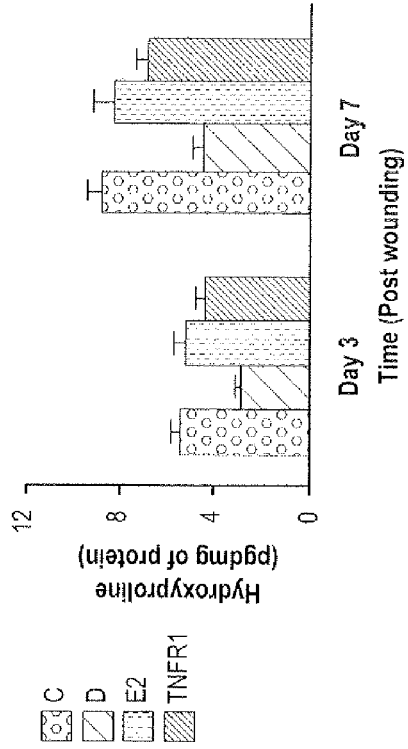
FIG. 2C is a chart showing relative collagen1 mRNA transcription in wounds at 3 days and 7 days in normal and diabetic rats, as well as in diabetic rats exposed to estradiol or TNF-α inhibitor.
Figure 2D:
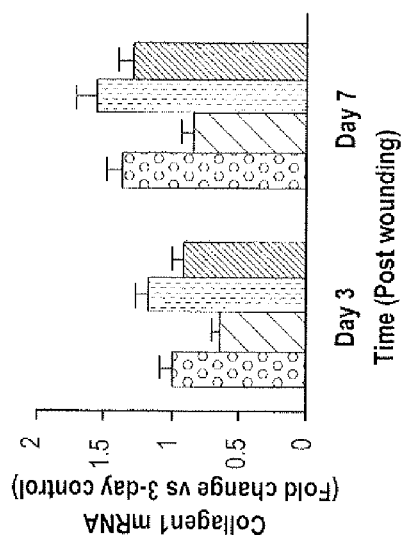
FIG. 2D is a chart showing relative hydroxyproline incorporation in wounds at 3 days and 7 days in normal and diabetic rats, as well as diabetic rats exposed to estradiol or TNF-α inhibitor.
Figure 2E:
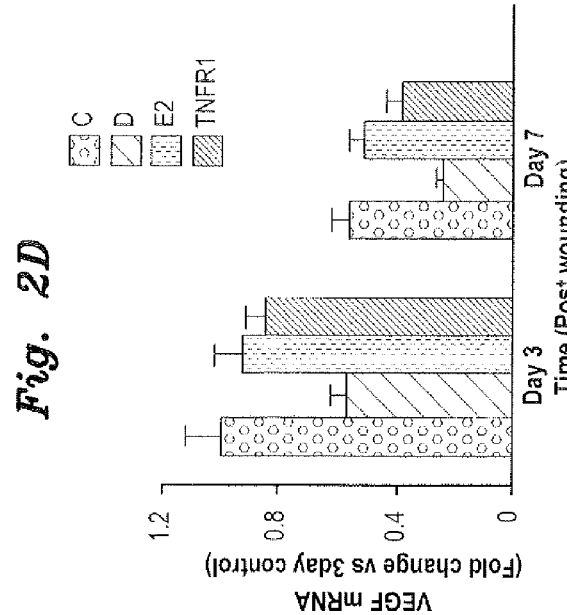
FIG. 2E is a chart showing fibroblast infiltration into wounds at day 3 and day 7 (as measured by vimentin detection) in normal and diabetic rats, as well as in diabetic rats exposed to estradiol or TNF-α inhibitor.

Prior to proper re-epithelialization, a new dermis must be formed, which involves deposition of new ECM (extracellular matrix) that is formed by, and serves as a substrate for, infiltrating cell migration. The deposition of fibronectin was initially analyzed in 3-day control and diabetic wounds using both RT-PCR and western blotting. The rate of deposition of these molecules was lower in diabetic wounds than in controls (FIGS. 2A and 2B). Accordingly, the two processes involved in tissue repair, namely, re-epithelialization and ECM deposition, appear to be suppressed as a function of diabetes. Delayed WH also suggests impairment in reformation of other ECM components, including collagen. This notion was advanced by examining collagen type I (Col I) mRNA expression during the course of WH. The resulting data documented a progressive increase in the gene expression of this extracellular-based molecule in control animals, but not in diabetic animals (FIG. 2C). Similar data were obtained by analysis of hydroxyproline, an indicator of collagen accumulation (FIG. 2D). Since fibroblasts represent the main source of ECM deposition and organization within the wound bed, the rate of infiltration of these cells was assessed at days 3 and 7 following wound induction. A diabetes-related decrease in the number of these cells was evident during the course of wound healing. Vimentin, a type of intermediate filament involved in cell migration in fibroblasts, decreased as a function of the diabetic state (FIG. 2E).

Figure 2F:
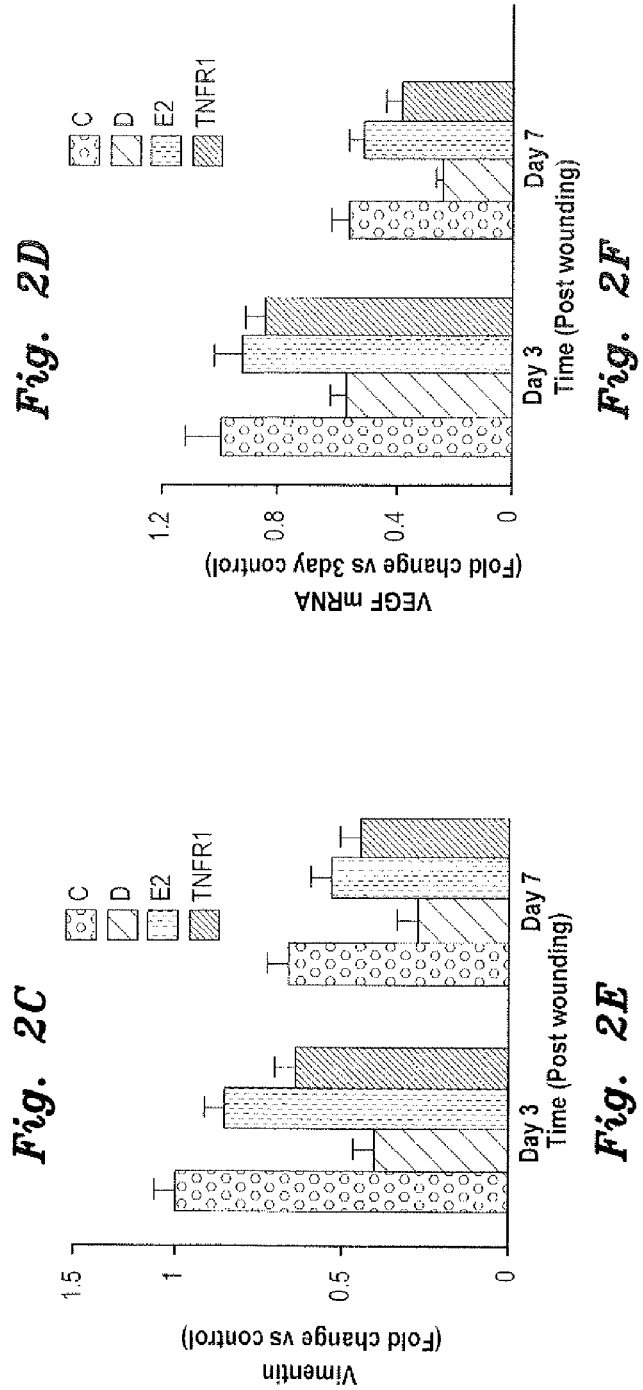
FIG. 2F is a chart showing relative VEGF mRNA transcription in wounds at 3 days and 7 days in normal and diabetic rats, as well as diabetic rats exposed to estradiol or TNF-α inhibitor.
Figures 2G, 2H:
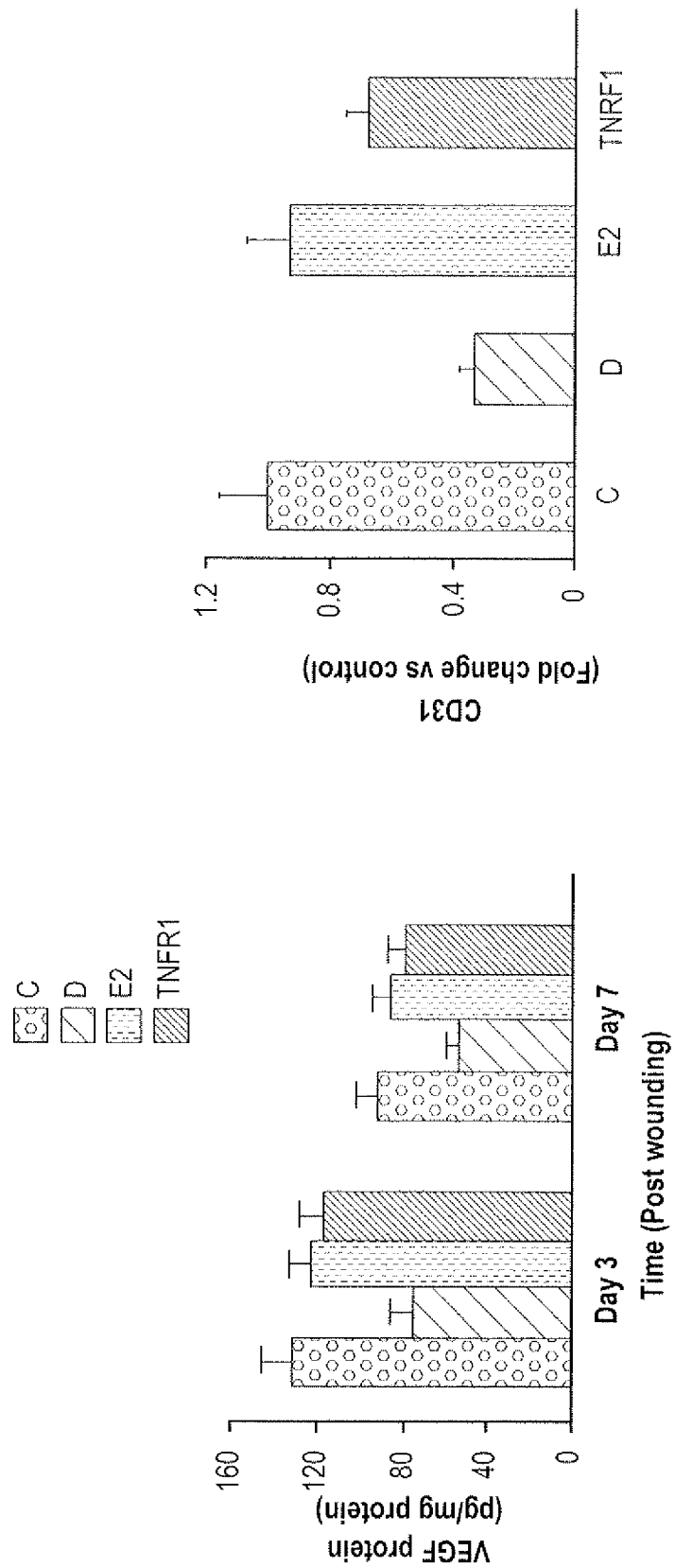
FIG. 2G is a chart showing relative VEGF protein in wounds at 3 days and 7 days in normal and diabetic rats, as well as diabetic rats exposed to estradiol or TNF-α inhibitor.
FIG. 2H is a chart showing relative number of endothelial cells (as measured by CD31 biomarker) in wounds at 7 days in normal and diabetic rats, as well as in diabetic rats exposed to estradiol or TNF-α inhibitor.

Angiogenesis also plays a critical role in maintaining newly formed granulation tissues. Accordingly, gene expression or the protein content of key angiogenic factors, such as VEGF, was examined at different time intervals during the course of WH. In uninjured skin, we noticed faint expression that was similar in both control and GK diabetic rats. However, an enhancement in VEGF protein and mRNA expression was evident in control animals at day 3 or 7 post-wounding, a phenomenon that was attenuated as a function of diabetes (FIGS. 2F and 2G). Moreover, skin wound-based neo-vascularization evaluated using von Willebrand Factor (vWF) (data not shown) or CD31, a marker of endothelial cells, was also suppressed on day 7 in diabetic wounds (FIG. 2H). Collectively, the above data are consistent with the concept that even slight hyperglycemia with evidence of insulin resistance in GK rats has deleterious effects on the healing process, as exemplified by impaired re-epithelialization, reduced collagen deposition, decreased angiogenesis and delayed wound closure.

EXAMPLE 3

This study focused on the role of the TGF-β signaling pathway in the impaired wound healing observed in diabetic GK rats. TGF-β1 is a multifunctional growth factor that regulates wound re-epithelialization, ECM formation, and granulation tissue formation during wound repair. The canonical TGF-β1 signaling pathways in diabetics during the course of WH were studied. Both TGF-β1 mRNA and protein levels were significantly lower in the 3 and 7 days diabetic wounds, compared with their corresponding controls (FIGS. 3A and 3B). To determine the cell types that showed reduced TGF-β, ELISA was performed on platelets, macrophages, and fibroblasts isolated from non-wounded control and GK diabetic rats. The aforementioned cells from the diabetic rats appear to secrete less TGF-β1, compared with their control counterparts (FIG. 3C). It should be noted that these cells were grown in culture under identical conditions, implying that the differences observed are inherent to the cells, rather than to external levels of glucose.

Further experiments were conducted to assess the canonical TGF-β signaling in diabetic wounds. TGF-β RII at the in RNA level on day 7 was markedly reduced in wounded tissues in the presence of diabetes (FIG. 3D). Moreover, a similar decrease in p-Smad-2 expression, an indicator of TGF-β-mediated activity, was also evident in this disease state (FIG. 3E). In contrast, wound levels of the negative regulators of TGF-β1/Smad signaling, including Smad 7 and β3-integrin, were augmented as a function of diabetes (FIGS. 3F and G).

EXAMPLE 4

Figure 4A:
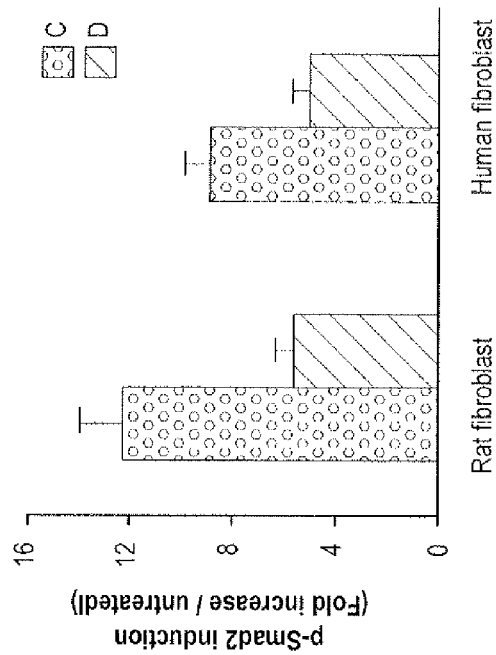
FIG. 4A is a chart showing relative TGF-β RII protein in normal and diabetic rat fibroblasts as well as normal and diabetic human fibroblasts.
Figure 4B:
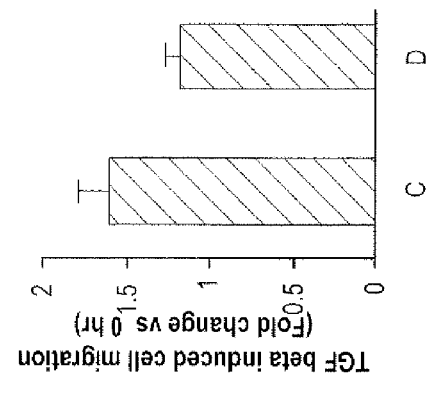
FIG. 4B is a chart showing the proportion of phosphorylated Smad2 in cells treated with TGF-β (compared with untreated) in normal and diabetic rat fibroblasts as well as normal and diabetic human fibroblasts.
Figure 4C:
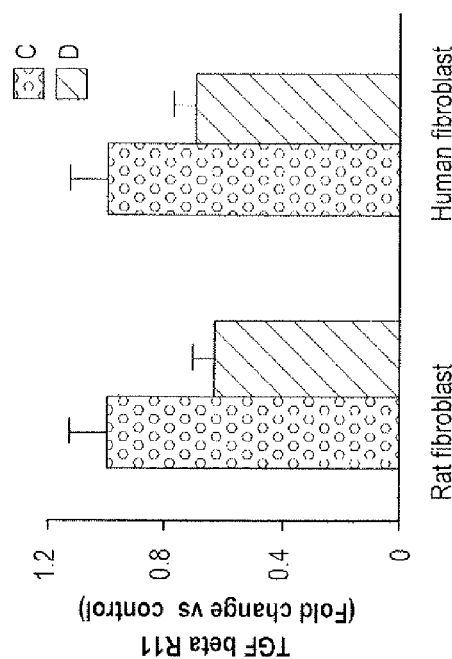
FIG. 4C is a chart showing the relative rate of Smad2/3 dinner localization in the nucleus in response to treatment with TGF-β (compared with untreated) in normal and diabetic rat fibroblasts.

To further investigate the cellular role of TGF-β signaling in the wound healing phenotype of type 2 diabetes, the levels of TGF-β RII and downstream Smad signaling in dermal fibroblasts isolated from control and GK rats, as well as from control and diabetic human subjects, were examined. The data revealed that cultured rat diabetic fibroblasts were resistant to TGF-β stimulation as assessed by the intracellular levels of p-Smad2, as well as other mediators that are known to be involved in the TGF-β1 action, including the ERK/GSK-3β/β-catenin pathway (data are only shown for TGF-β RII and p-Smad2). This phenomenon appears not to be species-specific, since similar findings were documented in HDF cell line (FIGS. 4A and B). Given that the degree of Smad nuclear localization reflects TGF-β receptor activity, the nuclear translocation of Smad2/3 in response to TGF-β in control and diabetic fibroblasts was determined. The data showed that nuclear translocation of Smad2/3 was suppressed in diabetic dermal fibroblasts, compared with corresponding control values (FIG. 4C).

Figure 4D:
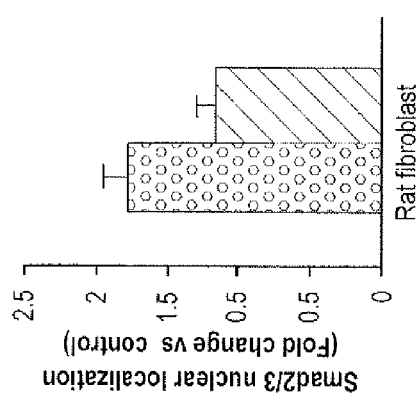
FIG. 4D is a chart showing the relative rate of cell migration in response to TGF-β in normal and diabetic rat fibroblasts.

To determine the mechanistic basis underlying the contribution of TGF-β resistance to impaired WH during diabetes, the regulation of in vitro cell migration and differentiation was assessed. For this purpose, a confluent fibroblast monolayer reaching confluence was subjected to a linear scratch with a pipette tip, and fibroblast migration into the wounded area was monitored. TGF-β1-induced cell migration at 24 hours was markedly reduced in diabetic fibroblast when compared to corresponding control values (FIG. 4D). In addition, TGF-β stimulation of collagen and of α-smooth muscle actin (α-SMA), a marker of myofibroblast differentiation, was also attenuated as a function of diabetes (FIG. 4E). The above abnormalities in TGF-β signalling were associated with a significant decrease in keratinocyte migration when these cells were incubated with a conditioned medium of fibroblast of type 2 diabetes (D-CM-F), as compared to corresponding control conditioned medium (C-CM-F) (e.g., migration distance, 138±12 μm for D-CM-F vs 179±14 for C-CM-F).

A number of intracellular molecules, including Smad7 and β3-integrin, have been shown to negatively regulate TGF-β/Smad-dependent signaling. Accordingly, the level of expression of these molecules was examined and they were found to be up-regulated in diabetic fibroblasts (FIG. 4F). Smad7 can be induced in response to the cytokines TNF-α/IL-1β, possibly by a NF-κB-dependent mechanism. This sequence of events was examined in diabetic cultured fibroblasts. The resulting data clearly show that TNF-α expression in connection with NF-κB activity is likewise elevated as a function of diabetes (FIG. 4O).

EXAMPLE 5

Figures 5A, 5B:
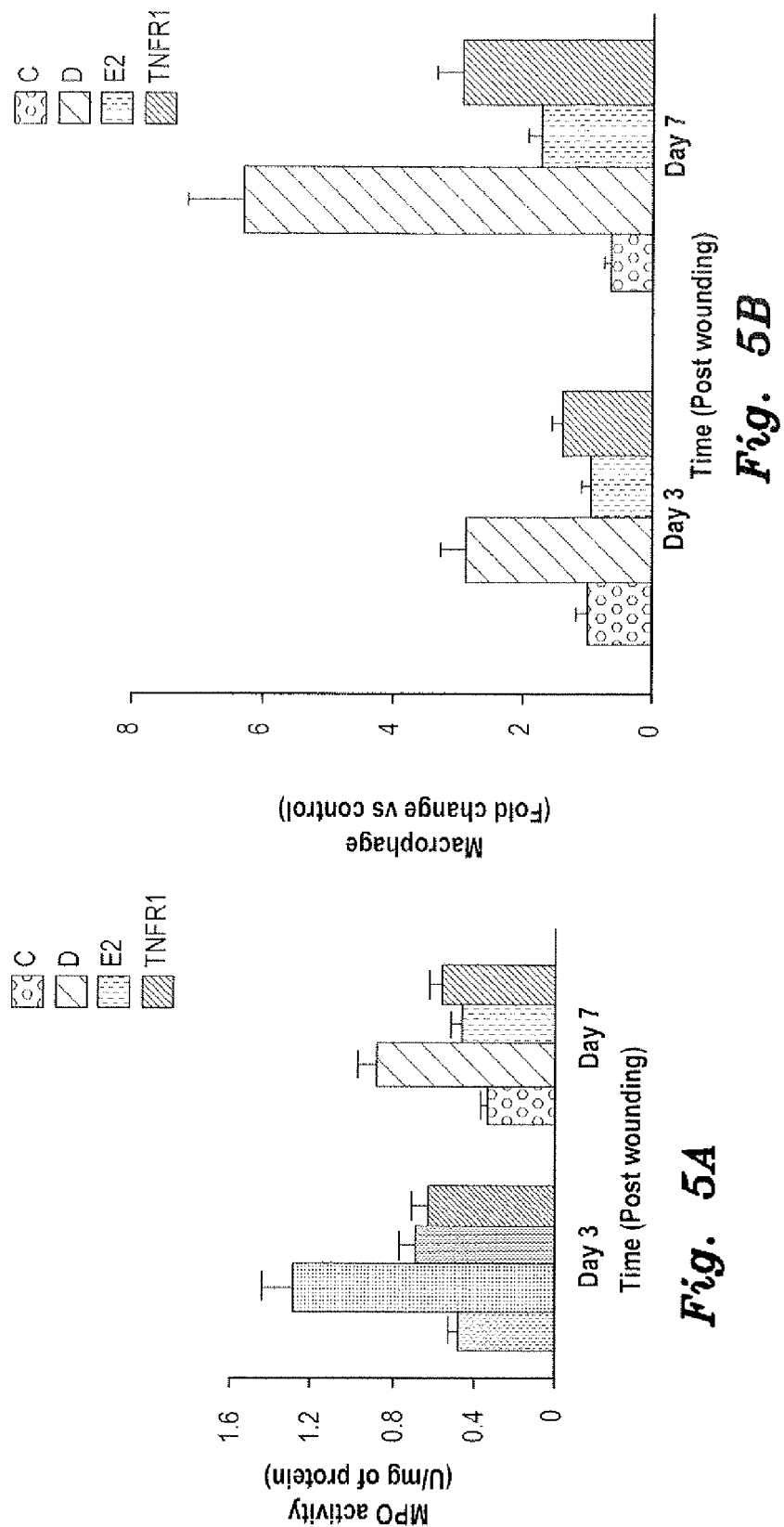
FIG. 5A is a chart showing myeloperoxidase (MPO) activity, a measure of neutrophil recruitment, at day 3 and day 7 in wounds of normal and diabetic rats, and in response to estradiol or TNF-α inhibitor.
FIG. 5B is a chart showing macrophage infiltration (visualized by CD68 marker) into wounds at day 3 and day 7 of normal and diabetic rats, and in response to estradiol or TNF-α inhibitor.
Figure 5D:
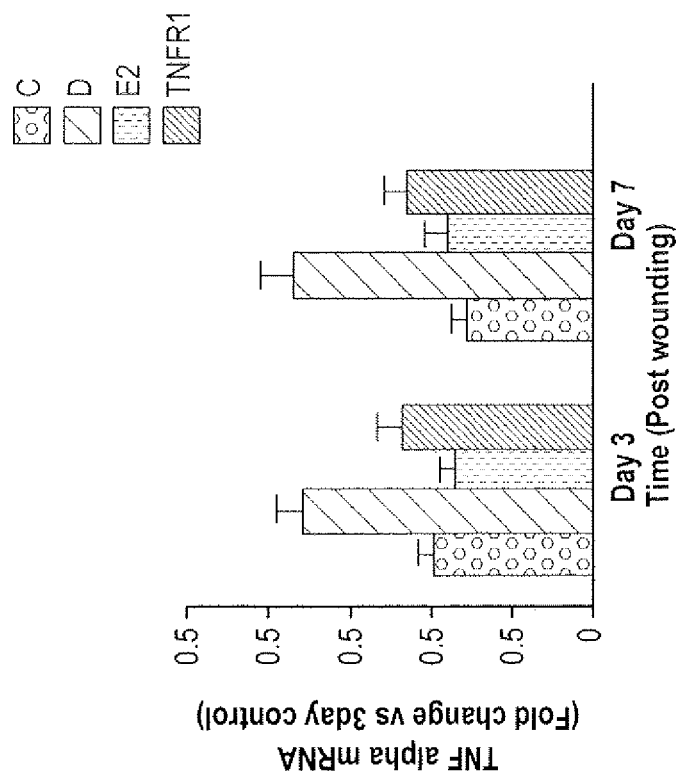
FIG. 5D is a chart showing transcription of TNF-α mRNA within wounds of normal and diabetic rats at day 3 and day 7, and in response to estradiol or TNF-α inhibitor.
Figure 5C:
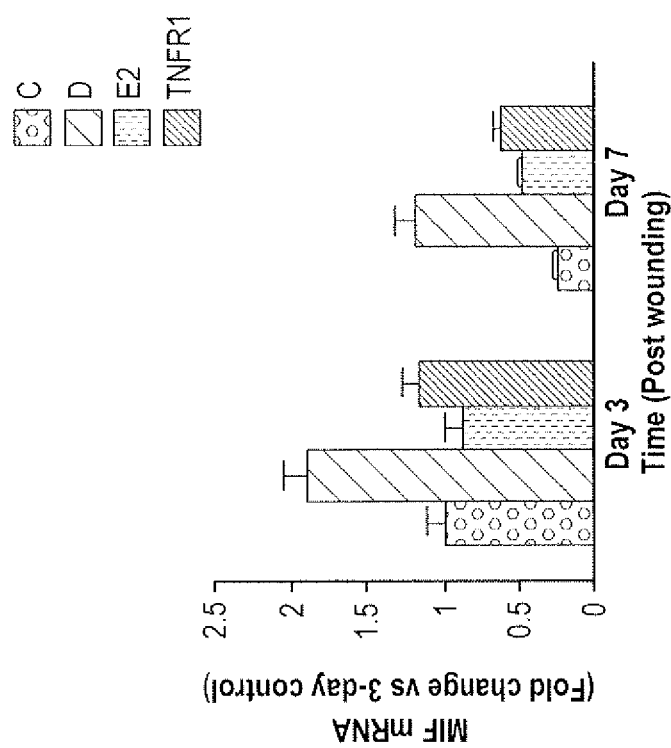
FIG. 5C is a chart showing transcription of macrophage inhibitory factor (MIF) mRNA in wounds of normal and diabetic rats at day 3 and day 7 in wounds of normal and diabetic rats, and in response to estradiol or TNF-α inhibitor.
Figure 5F:
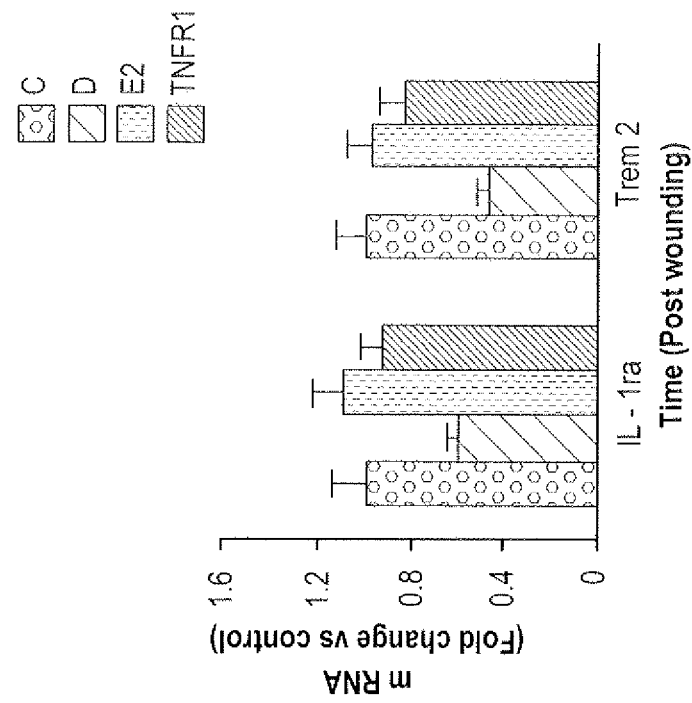
FIG. 5F is a chart showing transcription of IL-1a and Trem-2 mRNA, markers of anti-inflammatory macrophages, in wounds of normal and diabetic rats at day 3 and day 7 and in response to estradiol or TNF-α inhibitor.
Figure 5E:
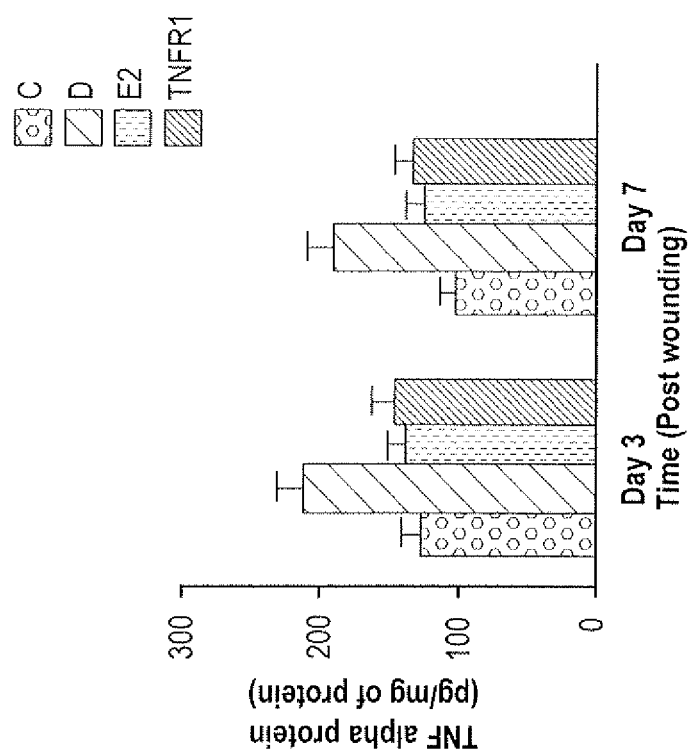
FIG. 5E is a chart showing expression of TNF-α protein within wounds of normal and diabetic rats at day 3 and day 7, and in response to estradiol or TNF-α inhibitor.

This study demonstrates that impaired resolution of inflammation within a wound microenvironment impacts skin tissue repair mechanisms and adversely affects TGF-β-mediated responses in a type 2 diabetes model. Cells of the monocyte-macrophage lineage undergo different forms of polarized activation in response to environmental signals, the extremes of which are called classic (M1) and alternative (M2). This plasticity-based characteristic enables macrophages to play a cardinal role in the orchestration and resolution of inflammation, and also to participate in wound repair and angiogenesis. The current study was initiated to characterize the pro-inflammatory M1 and the anti-inflammatory M2 macrophages within the diabetic wound microenvironment using spectrophotometric-, immunofluorescence-, ELISA-, and RT-PCR-based techniques. In this context, neutrophil recruitment exemplified by the activity of myeloperoxidase (MPO) was markedly exaggerated in diabetic wounds during the early and later stages of the healing process (FIG. 5A). Similarly, a marked increase in the number of macrophages, assessed with the use of antibody against CD68, was observed in 3 and 7 days diabetic wounds (FIG. 5B). The later findings were associated with increased expression of key M1-derived markers (e.g. TNF-α, MIF), both at the mRNA and/or protein level (FIG. 5C-E). In contrast, mRNA expression of M2-derived markers, exemplified by the IL-1ra, TREM2 (FIG. 5F), and TGF-β1, (FIGS. 3A and B), were markedly reduced in diabetic wounds. Interestingly, wounds retrieved from control animals exhibited a progressive time-dependent decrease in the rate of expression of the M1-related proinflammatory cytokines. This phenomenon appears to be attenuated in diabetic wounds. Indeed, the % of decrease in the levels of mRNA for MIF in the 7 days control and diabetic wounds, compared to 3 days counterpart, was 86% and 37%, respectively.

Delineating the molecular basis of this diabetes-related aberration in both inflammation resolution and macrophage polarization during the course of WH led us to assess NFκB/Rel dynamics. This redox-sensitive transcription factor is a pivotal player in inflammatory processes during immune responses. In addition, it is also a major target of the M1-related cytokines, including IL-1β- and TNF-α-mediated signaling pathways. Consistent with the above findings, the data in FIG. 5G confirmed that the DNA binding activity of the p65 subunit of NF-κB was increased in diabetics at day 3 and day 7 post-wounding.

EXAMPLE 6

This study demonstrates that ERT, when used in conjunction with PEG-sTNF-RI, accelerates wound closure, promotes inflammation, and enhances TGF-β signaling in a type 2 diabetes model. The current data clearly show that ERT resulted in a partial reversal of the diabetes-related decrease in the expression of wound M2 macrophage phenotype (FIGS. 2F and G, FIGS. 3A and B, FIG. 5F). Similarly, the up-regulation in M1 macrophage-derived markers, together with the resolution of inflammation within the diabetic wound microenvironment, was also normalized in response to ERT (FIG. 5C-E). This pro-resolving/M2 polarizing effect of ERT was recapitulated with the use of PEG-sTNF-RI, and it appears to be associated with a significant improvement not only in the deposition of ECM (FIG. 2A-D), but also in the healing process, both at the macroscopic and microscopic levels (FIGS. 1A and B). Finally, E2 and PEG-sTNF-RI were administered to GK rats in order to verify whether additive/synergistic effects on the healing process can be attained. Interestingly, our data clearly showed that combined treatment significantly improved wound closure and re-epithelialization when compared to GK rats treated with ERT or TNF-RI alone.

Figure 5G:
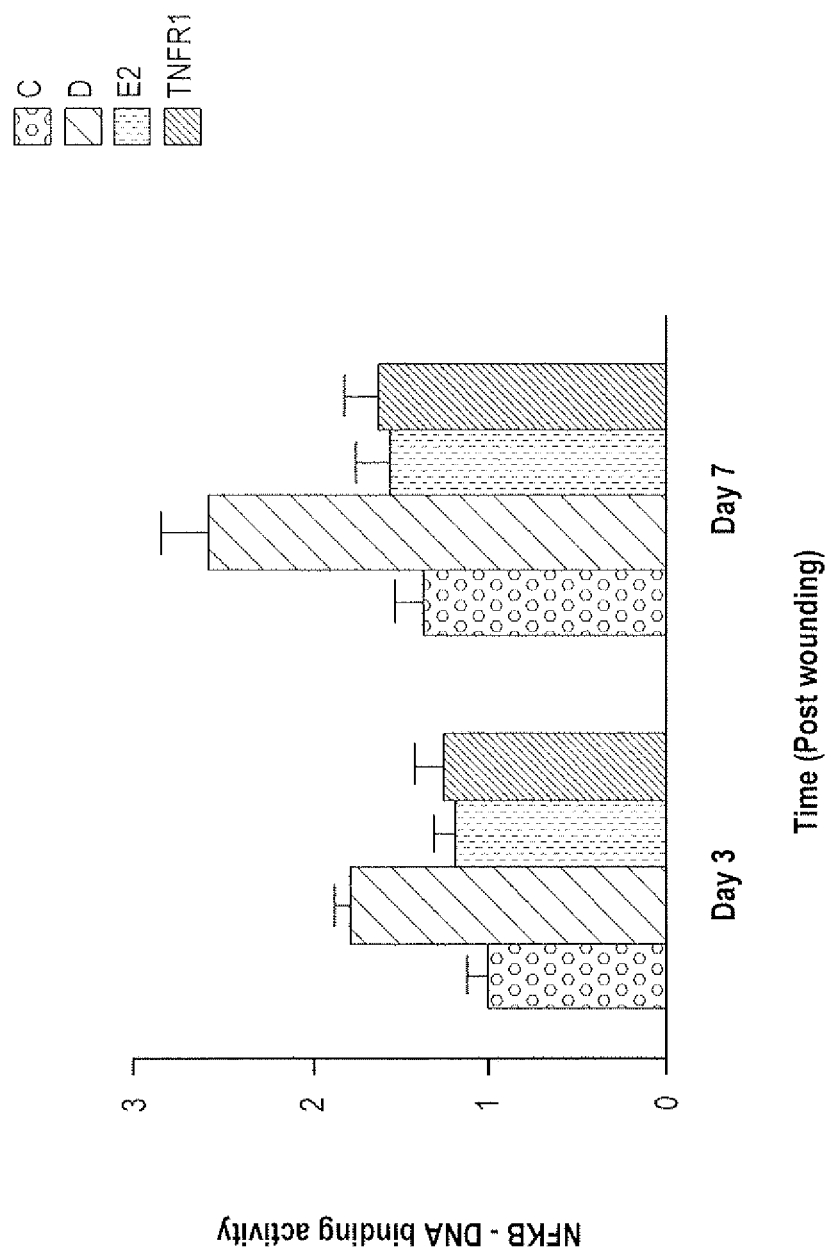
FIG. 5G is a chart showing NF-κB DNA binding activity in wounds of normal and diabetic rats at day 3 and day 7 and in response to estradiol or TNF-α inhibitor.

Since TGF-β1 is a key coordinator of WH and plays an important role in a variety of cellular responses, including cell migration, angiogenesis and ECM deposition, most of which were corrected in diabetic wounds by the institution of ERT or TNF-RI therapy, it was reasoned by the inventors that these pharmacological agents may also ameliorate diabetes-related impairment of TGF-β1-Smad signaling pathway. As shown in FIGS. 3D-3F, TGF-βRII expression in connection with phospho-Smad2, an indicator of positive TGF-β1 signaling, was augmented, whereas Smad7 levels were decreased in wounds from ERT and TNF-RI-treated diabetic rats (FIG. 3D-3F). This positive effect of ERT and TNF-RI on the tissue reparative process was associated with a significant decrease in NF-κB activity (FIG. 5G).

It is to be understood that the present invention is not limited to the embodiments described above, but encompasses any and all embodiments within the scope of the following claims.

We claim:

1. A method of treating diabetes-related impaired wound healing, comprising the steps of: administering an effective amount of estrogen replacement therapy to a diabetic patient in need thereof to promote wound healing, wherein said step of administering an effective amount of estrogen replacement therapy comprises administering an effective amount of β-estradiol; and administering an effective amount of a TNF-α inhibitor to a diabetic patient in need thereof to promote wound healing; whereby the estrogen replacement therapy and the TNF-α inhibitor exert an enhanced effect to promote healing of the wound, thereby accelerating wound closure and improving re-epithelialization;
wherein said effective amount of estrogen replacement therapy and said effective amount of a TNF-α inhibitor are administered subcutaneously;
wherein said step of administering an effective amount of a TNF-α inhibitor is administering an effective amount of PEG-sTNF-R1 to the diabetic patient; and wherein said step of administering an effective amount of PEG-sTNF-R1 comprises administering between 600 µg/kg of body weight and 900 µg/kg of body weight per week to the diabetic patient.

2. The method of treating diabetes-related impaired wound healing according to claim 1, further comprising the steps of: monitoring cytokine levels at the site of the wound; periodically obtaining samples of dermal fibroblasts from the site of the wound during wound healing; monitoring expression of tumor necrosis factor receptor proteins and levels of M1 and M2 macrophage phenotypes in the fibroblast samples; and adjusting dosage of the TNF-β inhibitor to maintain TNF-β activity at levels comparable to TNF-β activity in non-diabetic patients undergoing wound healing in order to promote sufficient cell proliferation for wound closure and normal wound healing time.

3. The method of treating diabetes-related impaired wound healing according to claim 1, further comprising the steps of monitoring estrogen levels in the diabetic patient during wound healing and adjusting the estrogen replacement therapy dosage to maintain an estrogen level comparable to estrogen levels in non-diabetic patients undergoing wound healing.

* * * * *